United States Patent [19]

Kataoka et al.

[11] Patent Number: 5,623,079

[45] Date of Patent: Apr. 22, 1997

[54] METHOD OF PREPARING N-FORMYL-L-ASPARTIC ANHYDRIDE

[75] Inventors: Takehiko Kataoka; Shinichi Kishimoto; Osahiro Sato, all of Kawasaki, Japan

[73] Assignee: Ajinomoto Co., Inc., Tokyo, Japan

[21] Appl. No.: 535,835

[22] Filed: Sep. 28, 1995

[30] Foreign Application Priority Data

Sep. 28, 1994 [JP] Japan .................................. 6-233425

[51] Int. Cl.$^6$ .................................................. C07D 307/66
[52] U.S. Cl. ............................ 549/253; 560/41; 562/565
[58] Field of Search .............................. 549/253; 560/41; 562/565

[56] References Cited

U.S. PATENT DOCUMENTS

| | | | |
|---|---|---|---|
| 5,183,937 | 2/1993 | Johnson | 562/608 |
| 5,358,186 | 10/1994 | Kataoka et al. | 241/24 |
| 5,393,915 | 2/1995 | Kataoka et al. | 560/41 |

FOREIGN PATENT DOCUMENTS 0121366  10/1984  European Pat. Off. .

*Primary Examiner*—Bernard Dentz
*Attorney, Agent, or Firm*—Oblon, Spivak, McClelland, Maier & Neustadt, P.C.

[57] ABSTRACT

The present invention provides an industrial method of producing N-formyl-L-aspartic anhydride from N-formyl-L-aspartic acid, formic acid and acetic anhydride with less residual formic acid than conventional methods.

8 Claims, 1 Drawing Sheet

[Figure 1]
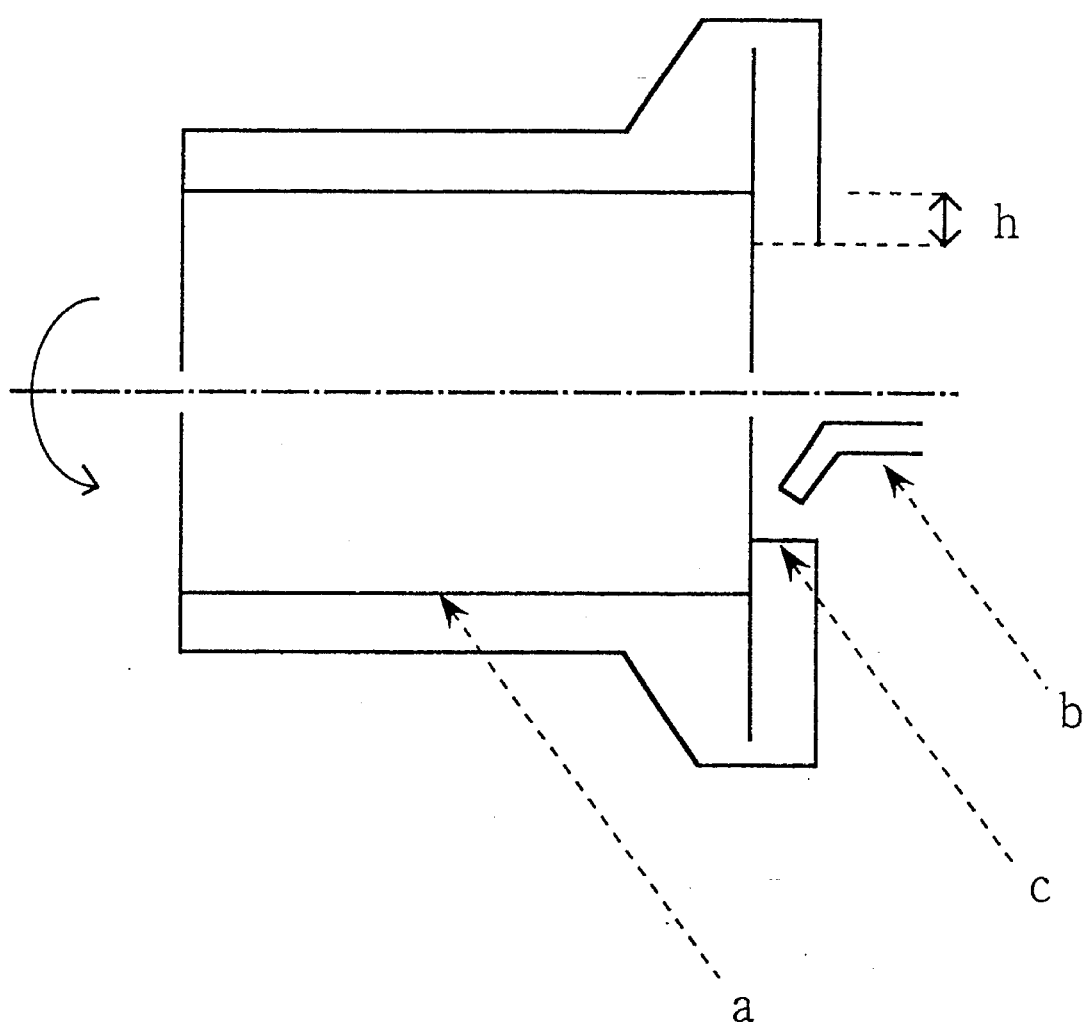

METHOD OF PREPARING N-FORMYL-L-ASPARTIC ANHYDRIDE

BACKGROUND OF THE INVENTION

1. Field of the Invention

The present invention relates to a method of preparing N-formyl-L-aspartic anhydride as an intermediate for the production of a dipeptide-based sweetener α-L-aspartylphenylalanine methyl ester. More particularly, the present invention relates to a method of preparing N-formyl-α-L-aspartyl-L-phenylalanine and N-formyl-α-L-aspartyl-L-phenylalanine methyl ester using N-formyl-L-aspartic anhydride as a starting material.

2. Discussion of the Background

N-formyl-L-aspartic anhydride (hereinafter referred to as FAA) is usually obtained by the reaction of N-formyl-L-aspartic acid with formic acid and acetic anhydride (hereinafter referred to as dehydration reaction). As such a reaction known is a reaction in which acetic acid and formic acid are employed in almost stoichiometric amounts based on aspartic acid (U.S. Pat. No. 4,526,985 and U.S. Pat. No. 4,810,816), which is problematic in that the yield is low as based on the amount of aspartic acid as the starting material.

In order to increase the yield of the dehydration reaction, it is necessary to use formic acid and acetic anhydride both in excessive amounts relative to the amount of aspartic acid. In such a case, a significant amount of unreacted formic acid remains at the end of the reaction.

When α-L-aspartyl-L-phenylalanine methyl ester (hereinafter referred to as α-APM) is produced as a final product, FAA is reacted subsequently with L-phenylalanine or its methyl ester (hereinafter referred to as PM) to yield N-formyl-α-L-aspartyl-L-phenylalanine (hereinafter referred to as F-α-AP) or its methyl ester (hereinafter referred to as F-α-APM), (hereinafter this reaction is referred to as condensation reaction). In such a condensation reaction, formic acid, if remains, inhibits the reaction and serves to reduce the yield of N-formyl-α-L-aspartyl-L-phenylalanine or its methyl ester (α form) relative to N-formyl-β-L-aspartyl-L-phenylalanine or its methyl ester (β form). There is no effective means to convert such a β form once produced to an α form in a subsequent step such as a deformylation step, and β-APM derived from the β form exhibits no sweetness. Accordingly, the reduction in the production ratio of the α form and the β form (α/β ratio) in the condensation process results in an increase in production loss, which leads to an increase in the amount of the starting materials and their reactants.

In an attempt to remove formic acid, a method of evaporating the dehydration reaction fluid to dryness has been described (U.S. Pat. No. 3,933,781). However, in view of the stability of the reaction products and the handling at an industrial scale, preferably the anhydride suspended in the dehydration reaction fluid is once subjected to solid/liquid separation, and then the isolated anhydrous crystal is subjected to the condensation reaction. It is also known that the isolation yield can be increased by conducting this separation in the presence of an aromatic hydrocarbon and/or halogenated hydrocarbon (JPA S51-91210).

Although it is preferable to separate the FAA from the reaction fluid by centrifugation in order to reduce as much as possible the residual solvent in FAA crystals after the separation, the centrifugation process involves problems that are characteristic of this system. For example, one problem is due to the fact that FAA crystals produced by the method mentioned above are in a form of a column having a diameter and height both as large as from 1 mm to 3 mm, resulting in a great intrinsic specific gravity which leads to quite rapid sedimentation. Accordingly, when the suspension is supplied to the filter whose basket has already started rotation, the filtration is completed instantly and therefore the separated FAA crystals which are formed on the basket at a certain thickness, i.e., the cake, shows local deposition without a uniformity in thickness. Such a condition affects the safety of the operation of the device, and makes it difficult to operate it continuously. As an attempt to avoid such unbalanced cake deposition, proposed is a method of supplying the suspension while rotating the basket at a quite low rate. However, a too low rotation rate results in the deposition of the cake concentrated in the place under the basket. Thus, the reduction in the rotation rate is also limited, and a rotation rate smaller than such limit fails to completely prevent unbalanced deposition.

Once such unbalanced deposition of the cake is formed at the time of fluid supply, subsequent filtration and dehydration should be conducted also at a very low rotation rate in view of safety. Accordingly, the cake ultimately obtained contains a large amount of fluid, i.e., a large amount of residual formic acid.

Also when washing the cake with a washing fluid, the efficiency of the washing varies by location depending on the thickness of the cake which results in another problem. On average, such variation causes extremely low washing efficiency when compared with the washing of a uniformly deposited cake. Considering the influence of the residual formic acid on the yield of the condensation reaction, it is a matter of course that the problems mentioned above become significant in cases of the production of α-APM as a final product.

On the other hand, when comparing the affinities of FAA with various solvent components in the dehydration reaction fluid (formic acid, acetic acid, acetic anhydride, aromatic hydrocarbon), the affinity for formic acid is especially high. Accordingly, the concentration of formic acid in the laminar film of the surface of the FAA crystals is higher than those in other regions of the reaction fluid. Therefore, in view of reducing the residual formic acid, it is desirable that the fluid is stirred vigorously when conducting the centrifugation to obtain a laminar film as thin as possible prior to the filtration. However, when a conventional centrifugation method is used, only a gentle fluidization such as through pumping of the suspension is achieved and then the filtration is conducted rapidly without an interval for obtaining a thinner laminar film.

Because of the various problems mentioned above, it is impossible to employ centrifugation to isolate FAA, and the separation is typically conducted using a pressurized plate filtration machine. However, such procedure involves complicated operations and is not suitable for large-scale production. Accordingly, in large scale production, a dehydration reaction not requiring the separation of FAA, i.e., the reaction using formic acid in a stoichiometric amount based on aspartic acid, should be employed in a practical stage.

SUMMARY OF THE INVENTION

Accordingly, one object of the present invention is to provide a method of producing FAA and separating the suspension wherein unbalanced FAA cake deposition is avoided, the safety of the operation and the dehydration capability are enhanced, a uniform deposition of the cake is achieved leading to an increase in the washing efficiency of the cake washing process, and the centrifugation condition capable of providing a thinner laminar film on the surface of FAA crystals just before the filtration is established, whereby FAA crystals are obtained containing only a small amount of residual formic acid.

A second object of the present invention is to provide a process for preparing F-α-AP or F-α-APM having a higher α/β ratio, i.e., at a high yield, by means of the reaction of the FAA crystals with L-phenylalanine or PM.

The present inventors have now found that when an FAA suspension is centrifuged, by supplying the first half amount of the suspension to be supplied at once, which is usually subjected to a low filtration resistance and thus filtrated rapidly, under a back pressure of 100 mmHg or higher, the unbalanced cake deposition can be avoided whereby the cake dehydration rate can be significantly increased, and a uniform thickness of the cake is obtained after the completion of the supply of the remaining suspension whereby the cake washing efficiency significantly is increased. In such a procedure, the back pressure means a higher pressure of the filtrate relative to the suspension to be supplied, and the back pressure value means the difference between the both pressures.

In addition, this procedure provides a prolonged residential period of the suspension in an extremely vigorous stirring condition due to the shearing force of the rotating basket, whereby enabling the filtration while avoiding the liquid phase adsorption of formic acid onto the surface of the FAA crystals.

It is also found that, by conducting the centrifugation in the condition mentioned above, FAA crystals containing a small amount of residual formic acid can be obtained, and the crystals can be reacted with L-phenylalanine or PM to produce F-α-AP or F-α-APM at a high yield while suppressing the formation of the β-form as a by-product.

BRIEF DESCRIPTION OF THE DRAWINGS

FIG. 1 shows a sectional view which outlines a centrifuge having a basket structure.

DETAILED DESCRIPTION OF THE PREFERRED EMBODIMENTS

The present inventors attained the present invention by applying the findings mentioned above to a practical process of the production of FAA, whereby the dehydration of FAA in the presence of excessive formic acid by centrifugation is enabled and the production loss in a later process due to the formation of the by-product β-form is significantly reduced.

Accordingly the present invention is a method of preparing N-formyl-L-aspartic anhydride (FAA) comprising:

reacting L-aspartic acid with acetic anhydride and formic acid in a molar amount of 1.05 times as large or larger than that of aspartic acid, to form a suspension containing N-formyl-L-aspartic anhydride, and centrifugating said suspension of N-formyl-L-aspartic anhydride while conducting the following steps:

(1) supplying said suspension to a separation device under a back pressure of 100 mmHg or higher;

(2) releasing said back pressure at a time when half or more of said suspension has already been supplied; and, (3) subsequently filtering and/or conducting dehydration of the cake while, if necessary, washing the cake. The amount of formic acid in the N-formyl-L-aspartic anhydride product is substantially reduced following the centrifugation step. Typically, greater than 50% of the formic acid is eliminated. Preferably, greater than 60% of formic acid is eliminated.

The reaction of N-formyl-L-aspartic acid with acetic anhydride and formic acid can be performed using conventional methods such as those described in JPA 46-1370 and U.S. Pat. No. 4,526,985 (incorporated herein by reference). Typically, the process consists of adding slowly, during a period of 5–8 hours, formic acid to the mixture of L-aspartic acid and acetic anhydride, in the respective amounts of 2.00–2.10 moles of acetic anhydride and 1.00–1.10 moles of formic acid per mole of aspartic acid at a temperature of up to 35° C., in the absence of a solvent, letting the reaction mixture stand for a period of 48–60 hours and isolating said anhydride of N-formyl-L-aspartic acid from the reaction mixture.

In addition, the present invention provides a method of preparing N-formyl-α-L-aspartyl-L-phenylalanine or N-formyl-α-L-aspartyl-L-phenylalanine methyl ester wherein crystals of N-formyl-L-aspartic anhydride thus obtained are dissolved or suspended in acetic acid and reacted with L-phenylalanine or L-phenylalanine methyl ester to yield N-formyl-α-L-aspartyl-L-phenylalanine.

In the separation of the anhydride according to the present invention, formic acid is employed in principle in an amount in excess of aspartic acid in the dehydration reaction. Considering the yield of the dehydration reaction, the molar amount is preferably 1.05 times as large or larger than that of aspartic acid. A catalyst may also be added in order to increase the yield of the dehydration reaction. An example of such a catalyst is the substance disclosed in U.S. Pat. No. 4,550,180 (incorporated herein by reference) such as magnesium acetate.

When the advantage in the separation of FAA mentioned above is desired, the back pressure employed in the present invention is at least 100 mmHg or higher, preferably 350 mmHg or higher, and most preferably 760 mmHg or higher, although it may vary depending on the centrifugal force. While a higher back pressure has a higher inhibitory effect on the unbalanced deposition, a much higher pressure causes a much lower rate of filtration which may lead to reduced performance of the device, and accordingly a pressure of 8000 mmHg or lower is preferable. The back pressure should be applied for the period during which at least a half of the suspension supplied in one separation can be supplied, and it is more preferable to supply the entire suspension under the back pressure. Although it is effective to apply the back pressure continuously for a certain period of time after the supply of the entire suspension, such continuous pressurization may prolong the time period required for one separation cycle and accordingly the optimum period should be determined considering the capacity of the performance of the separation device.

The back pressure is applied by, for example, (1) providing a valve in the outlet tube to reduce the flow rate of the filtrate, and (2) providing a device comprising duplicate baskets consisting of an inner and an outer one and a filter between them, in which the filtrate is allowed to flow on the outer basket and the water level of the filtrate when exiting the basket is set to the inside of the plane of the filter.

In method (1), when using a vertical centrifuge, the filtrate is allowed to remain in a space between the rotating basket and the outer casing, and the back pressure corresponding to the fluid surface and the fluid column of the valve is applied.

In method (2), the basket shown in FIG. 1 is employed. The device comprises a filter (a) and tube (b) for skimming the filtrate. During the separation, a back pressure corresponding to the difference in the height (h) between the filter level (a) and the water level (c) of the filtrate. The structure of the separation device having such a basket is disclosed in U.S. Pat. No. 3,943,056 and. U.S. Pat. No. 4,052,303 (incorporated herein by reference) and is also commercially available. When this device is employed in the present invention, the back pressure can be adjusted by adjusting the rotation rate of the basket and the insertion depth of the skimming tube.

FAA may be separated directly by separating the dehydration reaction fluid or after the addition of a solvent capable of reducing the solubility of FAA. Suitable solvents include aromatic hydrocarbons such as benzene, toluene, xylene, ethyl benzene and/or halogenated hydrocarbons such as chloroform and ethylene dichloride. Preferably, benzene or toluene is used.

FAA crystals thus obtained can be reacted with L-phenylalanine or L-phenylalanine methyl ester (PM) using conventional methods such as those described in U.S. Pat. No. 3,786,039 and U.S. Pat. No. 3,933,781, respectively (incorporated herein by reference). Typically, FAA crystals are dissolved or suspended in a solvent such as acetic acid and then reacted with L-phenylalanine which is in the form of a solid or PM which is dissolved in a solvent such as toluene.

By the method according to the present invention, the dehydration in the presence of excessive formic acid which is associated with the centrifugation of FAA as a step at an industrial scale is possible whereby increasing the dehydration yield is increased, while FAA crystals containing a small amount of residual formic acid can be used in the condensation step whereby the loss due to the formation of a β form as a by-product in a later step is reduced, thus providing a practically valuable method.

EXAMPLES

Having generally described this invention, a further understanding can be obtained by reference to certain specific examples which are provided herein for purposes of illustration only and are not intended to be limiting unless otherwise specified.

EXAMPLES 1 TO 2

A Peeler Centrifuge Model Hz100Si manufactured by Mitsubishi Chemical which is a centrifuge with a basket structure as shown in FIG. 1 (basket diameter: 1000 mm, Filtration area: 1.57 m$^2$) was used to conduct the separation test of a dehydration reaction fluid. The dehydration reaction fluid employed was a suspension obtained by admixing a solution mixture consisting of formic acid and acetic anhydride with magnesium acetate and L-aspartic acid to effect the dehydration reaction followed by the addition of toluene and then by cooling to 5° C. The molar ratio of formic acid to aspartic acid introduced for the reaction was 1.5. The concentrations of N-formyl-L-aspartic anhydride, formic acid, acetic acid and toluene in the reaction suspension were 16.0, 3.1, 26.8 and 49.9% by weight, respectively.

The entire volume of the suspension fed in one separation test was set at a constant 300 L, and the fluid was supplied in 50 L aliquots 4 times at the interval of 5 seconds. At the initiation of the fluid supply, a certain back pressure adjusted by means of selecting the basket rotation rate and the insertion depth of the skimming tube, and the basket rotation rate was adjusted at the highest rate (1400 rpm) at predetermined times after the 0th to 4th fluid supplies while further inserting the skimming tube whereby the back pressure was released prior to the subsequent separation process.

After the completion of the separation, the cake was washed with 100 L of toluene, and the rate of formic acid elimination was determined according to Formula 1.

Formula 1

Formic acid elimination rate [%] = {(formic acid content in cake before washing [wt %] − formic acid content after washing [wt %])/formic acid content in cake before washing [wt %]} × 100

The operational conditions and formic acid elimination rate in the separation tests are given in Table 1.

TABLE 1

| | Back Pressure [mmHg] | Rate of Suspension fed under back pressure based on total suspension fed | Formic Acid elimination [%] | Remarks |
| --- | --- | --- | --- | --- |
| Comparative Example | 0 | — | — | Operation impossible due to unbalanced cake |
| Comparative Example | 50 | ½ | 40 | Unbalanced cake |
| Comparative Example | 250 | ¼ | 24 | Severely unbalanced cake |
| Example 1 | 250 | ½ | 75 | |
| Example 2 | 250 | 1 | 91 | |

EXAMPLES 3 TO 4

To a solution mixture consisting of formic acid and acetic anhydride, first magnesium acetate was added and then L-aspartic acid was added in such an amount that the molar ratio of formic acid and aspartic acid was 1.3:1, whereby effecting the dehydration reaction. The concentrations of N-formyl-L-aspartic anhydride, formic acid and acetic acid in the reaction suspension after completion of the reaction were 32.7, 4.2 and 54.8% by weight, respectively. 150 L aliquots of this reaction suspension were separated by the two methods described below and each 100 L of acetic acid was used to wash the cake, whereby obtaining wet crystals of N-formyl-L-aspartic anhydride.

(1) Separation device: Peeler Centrifuge Model Hz100Si manufactured by Mitsubishi Chemical (Basket diameter: 1000 mm, Filtration area: 1.57 m$^2$) Condition: By adjusting the insertion depth of the skimming tube, 80 L of the suspension, which is about half of the entire suspension, was fed under a back pressure of 800 mmHg. Subsequently, the back pressure was released, and then the remaining suspension was fed prior to the cake washing followed by dehydration.

(2) Separation device: Top discharge vertical centrifuge (basket diameter: 1070 mm; filtration area: 1.38 m$^2$) Condition: In an attempt to avoid the unbalanced cake deposition, 30 L of the suspension was initially fed at a low rotation rate, but the suspension was filtrated only at the bottom of the basket. Then the remaining suspension was fed while manually adjusting the basket rotation rate within the range of from a low to a high rate. Nevertheless, the unbalance of the cake could not be avoided, and the dehydration after the cake washing could be conducted only at a rotation rate of as low as ¼ of the maximum rotation rate.

The content of formic acid in the wet crystal obtained in each of methods (1) and (2) was determined and the results are shown in Table 2.

The wet crystal thus obtained was then suspended in acetic acid and heated at 45° C., and L-phenylalanine in an equal molar amount relative to N-formyl-L-aspartic anhydride in the suspension was added to conduct the condensation reaction. The contents of N-formyl-α-L-aspartyl-L-phenylalanine and N-formyl-β-L-aspartyl-L-phenylalanine in the reaction fluid after the reaction were determined by HPLC, and the production ratio (α/β ratio) was calculated. The results are shown in Table 2.

The wet crystal was suspended again in acetic acid and kept at 25° C., and a solution of L-phenylalanine methyl ester in toluene was added in a molar amount of 0.97 relative to N-formyl-L-aspartic anhydride to effect the condensation reaction. The contents of N-formyl-α-L-aspartyl-L-phenylalanine methyl ester and N-formyl-β-L-aspartyl-L-phenylalanine methyl ester in the reaction fluid after the reaction were determined by HPLC, and the production ratio (α/β ratio) was calculated. The results are shown in Table 2.

TABLE 2

|  | Formic acid content in wet crystal [wt %] | Example 3 α/β ratio [—] | Example 4 α/β ratio [—] |
| --- | --- | --- | --- |
| (1) | 0.16 | 2.42 | 5.10 |
| (2) | 1.53 | 1.58 | 4.31 |

What is claimed as new and desired to be secured by Letters Patent of the United States is:

1. A method of preparing N-formyl-L-aspartic anhydride (FAA) comprising:

reacting L-aspartic acid with acetic anhydride and formic acid in a molar amount 1.05 times as large or larger than that of aspartic acid to form a suspension comprising N-formyl-L-aspartic anhydride, and centrifuging said suspension of N-formyl-L-aspartic anhydride in the presence or absence of an aromatic hydrocarbon to obtain a cake of FAA while:

(i) supplying said suspension to a separation device under a back pressure of 100 mmHg or higher;

(ii) releasing said back pressure at the time point when at least half or more of said suspension has been supplied; and (iii) subsequently filtering and/or dehydrating said cake, while optionally washing the cake.

2. The method according to claim 1, wherein said aromatic hydrocarbon is a solution mixture of at least one member selected from the group consisting of benzene, toluene and xylene.

3. The method according to claim 1, wherein said back pressure in step (i) is 350 mmHg or higher.

4. The method according to claim 1, wherein said back pressure in step (i) is 760 mmHg or higher.

5. The method according to claim 1, wherein said back pressure is released in step (ii) after completion of the supply of the entire amount of said suspension.

6. The method according of claim 1, wherein a solution mixture of an aromatic hydrocarbon and acetic acid is used as a washing fluid to wash said cake.

7. A method of preparing N-formyl-α-L-aspartyl-L-phenylalanine wherein crystals of N-formyl-L-aspartic anhydride obtained according to claim 1 are dissolved or suspended in acetic acid and reacted with L-phenylalanine.

8. A method of preparing N-formyl-α-L-aspartyl-L-phenylalanine methyl ester wherein crystals of N-formyl-L-aspartic anhydride obtained according to claim 1 are dissolved or suspended in acetic acid and reacted with L-phenylalanine methyl ester.

* * * * *